United States Patent
Casasanta, III

(10) Patent No.: US 7,745,143 B2
(45) Date of Patent: Jun. 29, 2010

(54) PLASMON RESONANCE BIOSENSOR AND METHOD

(75) Inventor: Vincenzo Casasanta, III, Woodinville, WA (US)

(73) Assignee: Plexera, LLC, Oriental, NC (US)

( * ) Notice: Subject to any disclaimer, the term of this patent is extended or adjusted under 35 U.S.C. 154(b) by 909 days.

(21) Appl. No.: 11/282,272

(22) Filed: Nov. 18, 2005

(65) Prior Publication Data

US 2006/0134669 A1    Jun. 22, 2006

Related U.S. Application Data

(60) Provisional application No. 60/629,491, filed on Nov. 19, 2004.

(51) Int. Cl.
*G01N 33/53* (2006.01)

(52) U.S. Cl. .................. 435/7.1; 435/7.2; 435/7.91; 435/7.92

(58) Field of Classification Search ............ 435/7.1, 435/7.2, 7.91, 7.92
See application file for complete search history.

(56) References Cited

U.S. PATENT DOCUMENTS

| | | | |
|---|---|---|---|
| 6,165,335 A | 12/2000 | Lennox et al. | |
| 6,406,921 B1 * | 6/2002 | Wagner et al. | 436/518 |
| 6,461,490 B1 | 10/2002 | Lennox et al. | |
| 6,478,939 B1 | 11/2002 | Lennox et al. | |
| 6,862,094 B2 | 3/2005 | Johansen | |
| 6,999,175 B2 | 2/2006 | Ivarsson | |
| 7,081,954 B2 * | 7/2006 | Sandstrom | 356/317 |
| 7,084,980 B2 | 8/2006 | Jones et al. | |
| 7,251,085 B2 | 7/2007 | Bahatt et al. | |
| 7,463,358 B2 | 12/2008 | Wolf et al. | |
| 2002/0044893 A1 * | 4/2002 | Corn et al. | 422/68.1 |
| 2002/0068813 A1 * | 6/2002 | Dragic et al. | 530/324 |
| 2004/0048311 A1 * | 3/2004 | Ault-Riche et al. | 435/7.1 |
| 2004/0258832 A1 | 12/2004 | Barklund et al. | |
| 2005/0014179 A1 | 1/2005 | Karlsson et al. | |
| 2005/0200845 A1 | 9/2005 | Nabatova-Gabain et al. | |
| 2006/0134669 A1 | 6/2006 | Casasanta | |
| 2006/0234265 A1 | 10/2006 | Richey et al. | |
| 2007/0081163 A1 | 4/2007 | Liang et al. | |
| 2007/0139653 A1 | 6/2007 | Guan et al. | |
| 2007/0222996 A1 | 9/2007 | Guan et al. | |
| 2009/0060786 A1 | 3/2009 | Kim et al. | |
| 2009/0060787 A1 | 3/2009 | Kim et al. | |

OTHER PUBLICATIONS

Patskovsky et al. (Sensors and Actuators B 2004 vol. 97, p. 409-414).*
Kim et al.; U.S. Appl. No. 12/339,017, filed Dec. 18, 2008.

* cited by examiner

*Primary Examiner*—Jacob Cheu
(74) *Attorney, Agent, or Firm*—Graybeal Jackson LLP

(57) ABSTRACT

A method of analyzing a sample comprising directing a beam of light to a spot on the surface of a microarray treated with the sample using a digital micromirror device, and observing the SPR spectral shift due to a chemical binding event. The digital micromirror device can be, for example, that used in Digital Light Processing (DLP). Such a device can selectively place a pixel of light onto a microarray such that each spot can be observed at millisecond intervals and the whole microarray can be sequentially scanned over a relatively short period. The SPR spectral shift for each spot can be measured as a function of time, thus producing SPR detection of molecular binding in an array format.

23 Claims, 4 Drawing Sheets

$\lambda_{t0}\ \lambda_{t1}\quad \lambda_{t2}\qquad \lambda_{t3}\qquad\qquad \lambda_{t4}\qquad\qquad \lambda_{t5}\ \lambda_{t6}$ $\Delta\lambda = \lambda_{tx} - \lambda_{t0}$ time, t

PLASMON RESONANCE BIOSENSOR AND METHOD

CROSS REFERENCE TO RELATED APPLICATIONS

This application claims priority to U.S. Ser. No. 60/629,491 entitled "Plasmon Resonance Biosensor and Method," which was filed Nov. 19, 2004 and is hereby incorporated by reference in its entirety.

All patents, patent applications, and publications cited within this application are incorporated herein by reference to the same extent as if each individual patent, patent application, or publication was specifically and individually incorporated by reference.

BACKGROUND

All patents, patent applications, and publications cited within this application are incorporated herein by reference to the same extent as if each individual patent, patent application, or publication was specifically and individually incorporated by reference.

The invention relates to detecting molecular binding events as well as photochemical spectral emission and/or absorption in a two-dimensionally discriminated manner such as, for example, in an array. The observation of molecular binding and affinity is a key element in biochemical and pharmaceutical research and development and analytical assays. In this field, the use of arrays is desirable in order to increase assay throughput and decrease the amount of expensive reagents consumed. Microarray technologies are commonly used in fluorescence, electrochemical, and mass spectrometry analytical instruments. However, microarray technologies based on surface plasmon resonance (SPR), which is a powerful method used for the detection of molecular affinity and binding, have developed more slowly. Array capable SPR systems are being developed that observe the angular shift in SPR upon binding using a charge couple device (CCD) camera and dual angular goniometers. In this approach, the change in reflectivity of the SPR sensor surface during a binding event is observed using the CCD output, which can be displayed as video gray level. Unfortunately, the use of dual goniometers to adjust the system to the resonance condition angle as well as to the linear portion of the SPR curve can produce a cumbersome and costly instrument. The other method of observing SPR is by wavelength absorption spectroscopy. In this approach, a molecular binding event is observed by a wavelength shift of the SPR absorption maximum. The observation of spatially discriminated or array organized binding/affinity events can be achieved by monitoring the spectra displayed at each position of a two-dimensional matrix or grid. However, there is still a need for simpler SPR sensing methods and instruments that will allow wide deployment in bioanalytics, biopharmaceutics, and proteomics with relatively compact size at low cost.

SUMMARY

One embodiment is a method comprising directing a beam of light to a spot on a microarray using a digital micromirror device and observing the SPR spectral shift due to a chemical binding event. The digital micromirror device can be, for example, that used in the Texas Instruments technology known as Digital Light Processing (DLP). Such a device can selectively place a pixel of light onto a microarray such that each spot can be observed at millisecond intervals and the whole microarray can be sequentially scanned over a relatively short period. The SPR spectral shift for each spot can be measured as a function of time, thus producing SPR detection of molecular binding in an array format. Preferably, the method further includes scanning a plurality of spots on a microarray. The system architecture allows for a low cost and simplistic design for an array based Surface Plasmon Resonance based analyzer for the detection of molecular binding events.

Chemical binding events typically include chemical binding pairs. The first component of the binding pair is immobilized on the microarray and the second component of the binding pair is bound to a chemical such as a protein. The chemical binding pairs can include, for example, a biotin/avidin pair, a hapten/antibody pair, an antigen/antibody pair, a peptide-peptide pair, a protein-DNA pair, a protein RNA pair, or complementary strands of DNA or RNA.

Other features and advantages will be apparent from the Detailed Description and from the claims.

DETAILED DESCRIPTION

Figure 1:
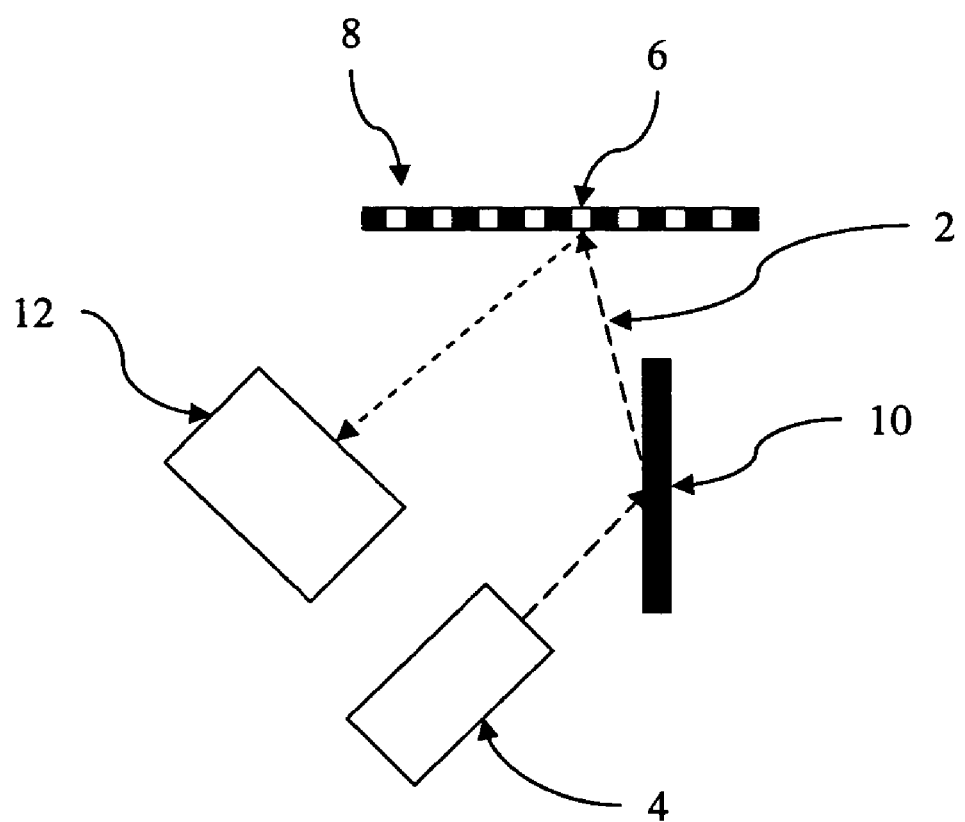
FIG. 1 is a schematic drawing of a method of directing a light beam on a microarray with a digital micromirror device.
Figure 2A:
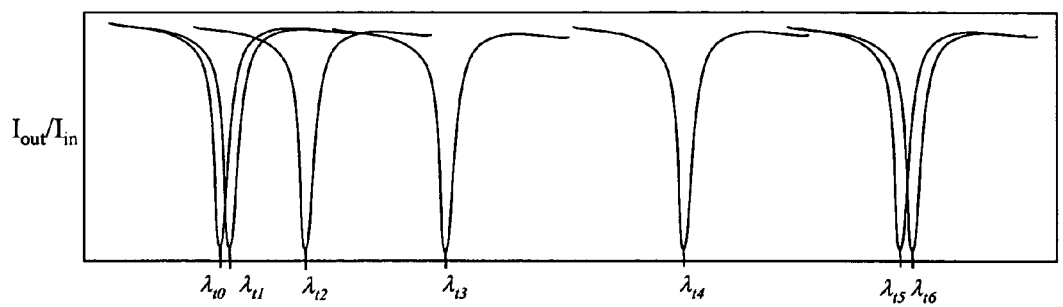
FIG. 2 contains schematic drawings of the output of the SPR method.
Figure 2B:
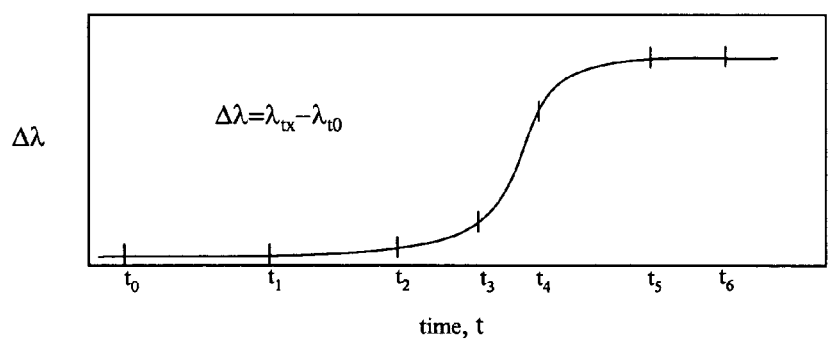
Figure 3:
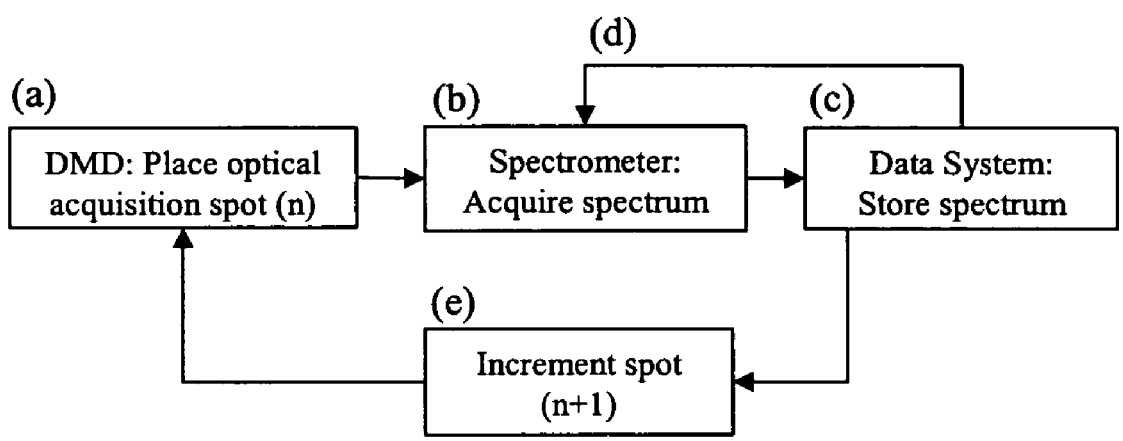
FIG. 3 is a schematic drawing of the function of the SPR method hardware and software.

Referring to FIG. 1, one embodiment is a method comprising directing a beam of light (2) from a light source (4) to a spot (6) on a microarray (8) using a digital micromirror device (10) and detecting the SPR spectral shift due to a chemical binding event at a detector (12). Preferably, the light passes through a prism or lens between the digital micromirror device (DMD) and the microarray. Typically, the prism or lens is in close contact with the backside of the microarray (i.e., the side of the microarray opposite that where the binding event occurs). The DMD can selectively place pixels (or pixel areas) of light onto a microarray such that multiple SPR spectral shifts can be measured for respective molecular binding events. If such events are observed at millisecond intervals the whole array can be sequentially addressed over time. Consequently the SPR spectral shift for each spot can be measured over time, thus producing molecular binding curves for the whole array as described in FIGS. 2a and 2b. FIG. 2a shows a schematic plot of SPR wavelength absorption spectral shifts at various states of a typical chemical binding event experiment. The "$\lambda_{r0}$" state is the initial condition without injection of the reactants. The spectrum at time "$\lambda_{r1}$" may represent the injection of the reactant. Several additional absorption maxima are labeled at various times, "$\lambda_{rx}$," and may represent, for example, further reactant injections or chemical binding events. One or more of the spectral shifts alone or in combination, for example from $\lambda_{r3}$ to $\lambda_{r4}$, may represent a chemical binding event. From this data, the relative absorption maximum shifts, $\Delta\lambda = \lambda_{rx} - \lambda_{r0}$, are calculated and plotted as a function of time to produce the binding curve shown in FIG. 2b. The microarray comprises, for example, of an array of thin film metal pads (i.e., spots) each with discreet and different probe molecules immobilized onto their surface. Over this surface is flowed the target molecule (reactant). Each array element will display its own distinct probe-target chemical binding event. A beam of broadband spectral light ranging from 200 nm to 2000 nm wavelengths is directed onto the digital micromirror device (DMD). The beam dimensions are large enough to cover the extent of the DMD chip. A pixel or pixel group on the DMD is assigned to each SPR sensor array element, each of which can be electronically accessed. When each SPR array element is sequentially illuminated (i.e., incremented through each spot on the microarray) each respective reflection spectrum is acquired. The spectral data from each spot is electronically stored for real-time or post acquisition analysis. The spectra are organized and binned sequentially such that the binding curves (mass accumulation versus time) are assembled. A schematic representation of an example of data acquisition for the method is shown in FIG. 3. In FIG. 3, a) a digital micromirror device (DMD) places the optical acquisition spot at a redetermined area on a microarray; b) a spectrometer acquires the spectrum of the predetermined area; c) a data system stores the spectrum; and either d) step b) and c) are repeated or e) a spot increment occurs by the DMD placing the optical acquisition spot on the next predetermined area. The chemical binding event can occur, for example, after the spectrum of each spot on the microarray has been acquired. In another embodiment, a chemical binding event can occur before incrementing to the next spot.

The digital micromirror device can be, for example, that used in the Texas Instruments technology known as Digital Light Processing (DLP). In one example, an microarray of approximately 1000 spots is imaged using a DMD, which includes a 36×28 microarray (1008 spots) that corresponds to an illumination allowance of a 28×28 pixels per spot for a 768×1024 (SVGA) DMD engine. If illumination intensity is sufficient, grating-CCD spectrometer technology allows spectrum acquisition every 1 millisecond, which allow the whole microarray to be imaged in about 1 second. In many embodiments, 100-1000 spots on a microarray can be imaged (i.e., interrogated). In other embodiments, the microarray spots comprise Au or Ag having thickness ranging from 10 nm to 200 nm.

Chemical binding events typically include chemical binding pairs. The first component of the binding pair is immobilized on a spot of the microarray and the second component of the binding pair is bound to a chemical such as a protein. During the assay, the second component is introduced to the microarray by, for example, printing or solution flooding, which allows the second component to come into contact with the first component to initiate the binding event and produce a complex. The chemical binding pairs can include, for example, a biotin/avidin pair, a hapten/antibody pair, an antigen/antibody pair, a peptide-peptide pair, or complementary strands of DNA or RNA. In all embodiments, a third chemical component may bind the complex of the first component and second component. The first component can be immobilized by reaction with a first functional group bound to the microarray surface. The first functional group may be any chemical moiety that can react with the first component of the binding pair. Depending on the composition of the first component of the binding pair, the first functional group may include, for example, an amine, a carboxylic acid or carboxylic acid derivative, a thiol, a maleimide, biotin, a hapten, an antigen, an antibody, or an oligonucleotide. The first functional group itself may be bound to the surface of the microarray through a second functional group that forms a covalent bond with the spots of the microarray. Preferably, the first functional group is biotin, the second functional group is a thiol, and the spots of the microarray each comprise gold.

Another embodiment is an SPR array reader, comprising: a) a light source; b) a digital micromirror device; c) a hemispherical prism; and d) a detector. The light source supplies light to the DMD and the hemispherical prism couples light from the DMD to a microarray. The detector detects the light reflected from the microarray (i.e., the SPR signal).

Figure 4:
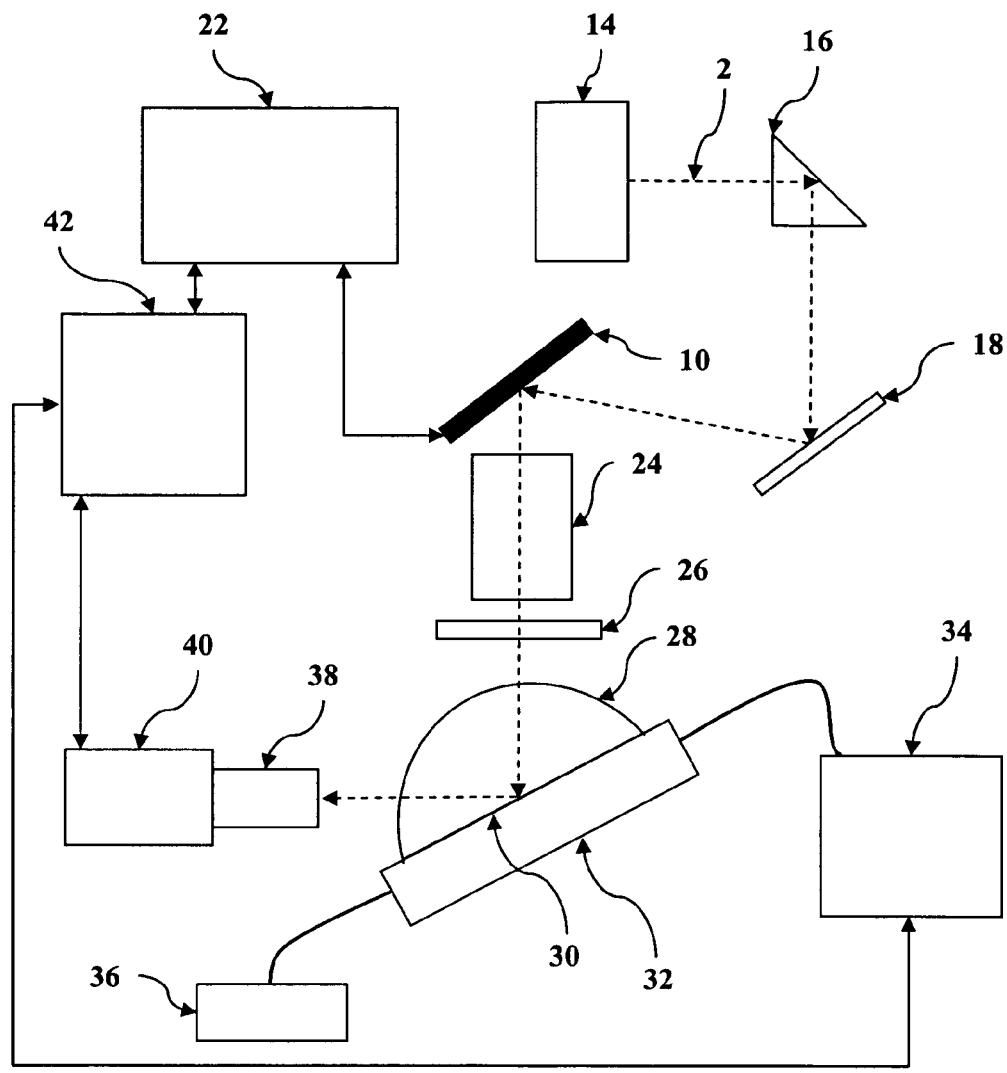
FIG. 4 illustrates an SPR microarray imager including and digital micromirror device.

In one embodiment, referring to FIG. 4, the SPR array reader comprises: a) a polychromatic broadband light source (14); b) a cooled dichroic mirror (16); c) a fold mirror (18); d) a digital micromirror device (10); e) a digital micromirror device controller (22); f) multiple element imaging optics (24); g) a polarizer (26); h) a hemispherical lens (28); i) a flat surface for a microarray (30); j); a flow cell assembly (32); k) a fluid pump (34); l); a fluid collector (36); m) detector input optics (38); n); a spectrometer (40); and o) a computer control system (42) that controls the DMD controller, the fluid pump, and the spectrometer and collects data from the spectrometer. Double headed arrows represent data and/or control paths to and from the computer control system (40) and the DMD controller (22).

The broadband light source (14) provides continuous illumination (i.e., a light beam (2)) of uniform intensity over, for example, a 3-4 $cm^2$ area with a wavelength band from 200 nm to 1200 nm using, for example, a Xe or W-halogen lamp and parabolic reflectors. In some cases the radiation may need to be filtered to eliminate certain wavelengths from the biological systems of interest, which may be accomplished, for example, with a dichroic "cold" mirror (16).

The input light is reflected by a fold mirror (18) onto the DMD (10). The DMD (10) is responsible for discriminating individual spots onto a microarray that may range from 10 μm to 1 mm in dimension. The individual spots are sequentially illuminated by an algorithm programmed into the DMD device controller (22). The reflected and spatially discriminated radiation is imaged onto a microarray through appropriate multi-element imaging optics (24) and a polarizer (26), which polarizes the light to produce a surface plasmon polariton. The light is coupled to the microarray by a truncated hemispherical prism (28) which is index matched to the substrate of the microarray.

The microarray is mounted on a flat surface (30) using an index matching fluid and a pressure clamped mount integrated into a flow cell assembly (32). The flow cell (32) is responsible for directing fluid analyte to the surface of the microarray whereby the SPR activity is optically monitored. The fluid analyte is delivered to the flow cell assembly by a fluid pump (34) and is collected after the flow cell (32) at a fluid collector (36).

The angle of incidence (angle between the input light ray and the normal vector to the microarray plane) may be adjusted by mounting the hemispherical prism and flow cell assembly on a precision rotation stage. The reflected output ray is directed by appropriate detector input optics (38) into a spectrometer (40). The spectrometer (40) may be mounted on a precision rotation-stage to facilitate the reflected light ray input. Typically, the spectrometer (40) comprises a grating and photodiode array or charge couple device (CCD) and allows for spectral acquisition at a rate of 1 spectrum per 1 millisecond.

The DMD is programmed by the computer control system (42) to place a sequential pixel group array of the input light beam onto a microarray mounted on the flat surface (30). The spot size, pitch, and beam dwell time are specified by the user. This same data is sent to a program which controls the acquisition parameters of the spectrometer (42) and synchronizes it with the DMD (10). The flow for this algorithm is shown in FIG. 3. If a spectrum is acquired for each spot every 1 millisecond then the binding event progression for a 1000 spot array is acquired is 1 second. In the simplest data analysis routine, the spectrum from each 1 second increment for each spot is stored for post processing. The post processing routine calculates the ratio of the output spectrum to the input spectrum and tabulates the absorption spectrum, it then finds the local minimum wavelength of each absorption spectrum and reports this value to a table. The tabulated series of local minima values are then subtracted from the initial wavelength minimum value and are plotted as a function of time to assemble the binding curves for each spot (FIG. 2b). The initial time value is dictated by the flow control cell system where the user defines the volume, flow rate, and duration of the injection of analyte into the flow cell (32). The fluid pump (34) provides for multiple analytes and a $10^7$ flow rate range control for both high rate flushing and minute introduction of picomolar concentration solutions.

Other embodiments are within the following claims.

What is claimed is:

1. A method for analyzing a sample comprising:
   (a) providing a microarray comprising a surface having a plurality of discrete locations, each of which includes a first member of a chemical binding pair and is associated with a surface plasmon resonance;
   (b) irradiating the discrete locations on the surface of the microarray with a light beam using an apparatus comprising a light source, a digital micromirror device, and a prism or lens located between the digital micromirror device and the surface of the microarray;
   (c) contacting the surface of the microarray with a sample comprising a second member of the chemical binding pair, whereupon, in at least one of the discrete locations, the second member of the chemical binding pair binds to the first member of the chemical binding pair on the surface of the microarray and causes a spectral shift in the surface plasmon resonance associated with the discrete location where the chemical binding occurs; and
   (d) detecting the surface plasmon resonance spectral shift associated with each location as a function of time therefore providing surface plasmon resonance detection of chemical binding with said sample in an array format.

2. The method according to claim 1 wherein the surface has at least 100 discrete locations.

3. The method according to claim 1 wherein the surface has at least 1000 discrete locations.

4. The method according to claim 1 wherein each discrete location comprises a thin metal pad on which the first member of the chemical binding pair is immobilized.

5. The method according to claim 1 wherein the apparatus comprises a hemispherical prism.

6. The method according to claim 1 wherein the light source comprises a polychromatic broadband light source that emits light having wavelengths in the range of 200 nm to 2000 nm.

7. The method according to claim 1 wherein the first member of the specific binder pair comprises a first functional group that reacts with the surface of the microarray at the discrete location to immobilize the first member on the surface of the microarray at the discrete location.

8. The method according to claim 7 wherein the first functional group is selected from the group consisting of an amine, a carboxylic acid or derivative thereof, a thiol, a maleimide, a biotin, a hapten, an antigen, an antibody, an oligonucleotide, and combinations thereof.

9. The method according to claim 7 wherein the first functional group immobilizes the first member of the chemical binding pair on the surface of the microarray through a second functional group that forms a covalent bond with the surface of the microarray at the discrete location.

10. The method according to claim 9 wherein the first functional group is biotin, the second functional group is a thiol, and the surface of the microarray at the discrete location comprises gold.

11. The method according to claim 1 wherein the surface of the microarray at the discrete location comprises a third functional group that reacts with the first member of the specific binder pair to immobilize the first member on the surface of the microarray at the discrete location.

12. The method according to claim 11 wherein the third functional group is selected from the group consisting of an amine, a carboxylic acid or derivative thereof, a thiol, a maleimide, a biotin, a hapten, an antigen, an antibody, an oligonucleotide, and combinations thereof.

13. The method according to claim 11 wherein the third functional group immobilizes the first member of the chemical binding pair on the surface of the microarray through a fourth functional group that forms a covalent bond with the first member of the chemical binding pair.

14. The method according to claim 13 wherein the third functional group is biotin, the second functional group is a thiol, and the surface of the microarray at the discrete location comprises gold.

15. The method according to claim 1 wherein the chemical binding pair comprises a biotin/avidin pair.

16. The method according to claim 1 wherein the chemical binding pair comprises a hapten/antibody pair.

17. The method according to claim 1 wherein the chemical binding pair comprises an antigen/antibody pair.

18. The method according to claim 1 wherein the chemical binding pair comprises a peptide/peptide pair.

19. The method according to claim 1 wherein the chemical binding pair comprises complementary strands of DNA.

20. The method according to claim 1 wherein the chemical binding pair comprises complementary strands of RNA.

21. The method of claim 1, wherein the digital micromirror device periodically addresses a sequence of the discrete locations.

22. The method of claim 21, wherein detecting a spectrum shift is performed by collecting non-imaged light from the discrete locations with a spectrometer.

23. The method of claim 1, wherein the microarray surface is a two-dimensional surface and the plurality discrete locations are disposed across the microarray surface in a two-dimensional array.

* * * * *